United States Patent
Araki et al.

(10) Patent No.: US 10,866,169 B2
(45) Date of Patent: Dec. 15, 2020

(54) METHOD FOR RECOVERING RARE CELLS AND METHOD FOR DETECTING RARE CELLS

(71) Applicant: Konica Minolta, Inc., Tokyo (JP)

(72) Inventors: Jungo Araki, Fuchu (JP); Kumiko Hoshi, Tama (JP)

(73) Assignee: KONICA MINOLTA, INC., Tokyo (JP)

( * ) Notice: Subject to any disclaimer, the term of this patent is extended or adjusted under 35 U.S.C. 154(b) by 483 days.

(21) Appl. No.: 14/436,300

(22) PCT Filed: Oct. 15, 2013

(86) PCT No.: PCT/JP2013/078006
§ 371 (c)(1),
(2) Date: Apr. 16, 2015

(87) PCT Pub. No.: WO2014/061675
PCT Pub. Date: Apr. 24, 2014

(65) Prior Publication Data
US 2015/0276564 A1    Oct. 1, 2015

(30) Foreign Application Priority Data

Oct. 17, 2012  (JP) ................. 2012-229770

(51) Int. Cl.
*G01N 1/30* (2006.01)
*C12M 1/00* (2006.01)
*B01L 3/00* (2006.01)

(52) U.S. Cl.
CPC .......... *G01N 1/30* (2013.01); *B01L 3/502761* (2013.01); *C12M 47/04* (2013.01); *B01L 2200/0668* (2013.01); *B01L 2300/0816* (2013.01); *B01L 2300/0877* (2013.01); *B01L 2400/0409* (2013.01); *B01L 2400/0487* (2013.01)

(58) Field of Classification Search
CPC .................. G01N 1/30; C12M 47/04
See application file for complete search history.

(56) References Cited

U.S. PATENT DOCUMENTS

| | | | |
|---|---|---|---|
| 2008/0138248 A1* | 6/2008 | Viovy | B01L 3/502707 422/400 |
| 2011/0027771 A1* | 2/2011 | Deng | C12Q 1/6806 435/2 |
| 2011/0189721 A1 | 8/2011 | Deutsch | |
| 2013/0035257 A1* | 2/2013 | Yu | C12N 11/04 506/11 |

FOREIGN PATENT DOCUMENTS

| | | |
|---|---|---|
| JP | 07-504570 A | 5/1995 |
| JP | 2001238663 A | 9/2001 |
| JP | 2003235539 A | 8/2003 |
| JP | 2006122012 A | 5/2006 |
| WO | 2006046490 A1 | 5/2006 |
| WO | 2011108454 A1 | 9/2011 |

OTHER PUBLICATIONS

Written Opinion of the International Search Authority and English translation.
International Search Report dated Dec. 17, 2013 for PCT/JP2013/078006 and English translation.
Extended European Search Report dated May 6, 2016; Application No./Patent No. 13846279.1-1371 / 2910642 PCT/JP2013078006; Applicant: Konica Minolta, Inc.; Total of 8 pages.
Office Action dated Aug. 17, 2018 from corresponding European Application No. EP 13846279.1.

* cited by examiner

*Primary Examiner* — Teresa E Knight
(74) *Attorney, Agent, or Firm* — Lucas & Mercanti, LLP (57) ABSTRACT

An object of the present invention is to provide a method of detecting rare cells in which, upon spreading a cell suspension in a flow path formed on a microchamber chip, the loss of rare cells is reduced by improving the cell recovery rate. The present invention provides a method of detecting rare cells from a cell suspension by using a cell-spreading device 10 comprising a microchamber chip 1, a flow path-forming frame 2, an inlet port 3, and an outlet port 4; and a method of recovering rare cells comprising: the step (X) of introducing a cell suspension to a flow path 5 via the inlet port 3 so as to spread cells in the flow path 5 on the microchamber chip 1; and the step (Y) of storing the cells spread in the flow path 5 on the microchamber chip 1 in microchamber 6s by intermittent liquid feeding.

18 Claims, 5 Drawing Sheets

METHOD FOR RECOVERING RARE CELLS AND METHOD FOR DETECTING RARE CELLS

CROSS REFERENCE TO RELATED APPLICATION

This Application is a 371 of PCT/JP2013/078006 filed on Oct. 15, 2013 which, in turn, claimed the priority of Japanese Patent Application No. JP2012-229770 filed on Oct. 17, 2012, both applications are incorporated herein by reference.

TECHNICAL FIELD

The present invention relates to a method of recovering and detecting rare cells from cells contained in a cell suspension spread in a flow path on a microchamber chip by using a cell-spreading device comprising the microchamber chip.

BACKGROUND ART

Circulating tumor cells [CTCs], circulating vascular endothelial cells [CECs], circulating vascular endothelial precursor cells [CEPs], various stem cells and the like (hereinafter, these cells are collectively referred to as "rare cells") are cells that extremely rarely exist in the whole blood depending on the pathological condition. Although it is obvious that detection of such rare cells is clinically useful, the detection is extremely difficult. In recent years, various separation methods have been applied in an attempt to perform the detection and various products have been commercialized; however, in any of these cases, because of the rarity of the subject, it is important to evaluate the results and effectiveness of the detection (the loss of rare cells and the presence/absence of contamination with unwanted cells).

For instance, in an examination of whether or not a rare cell of interest exists in a sample such as collected blood, the presence or absence of the cell of interest in a cell suspension such as a blood-derived sample can be determined by planarly spreading the cell suspension and then analyzing all of the spread cells.

For example, Patent Document 1 discloses a microdevice for cellular tissue body. On the surface thereof, "cell holding chambers" are formed, and a cellular tissue body can be formed by culturing cells (such as primary stem cells) contained in the cell holding chambers while perfusing a culture medium to a flow path.

In cases where this microdevice for cellular tissue body is used to planarly spread a cell suspension, it is expected that enough cells cannot be recovered in the cell holding chambers by simple addition of the cell suspension thereto and that many cells consequently remain outside the cell holding chambers. In addition, immediately after the start of perfusion culture, those cells remaining outside the cell holding chambers may be discharged from the microdevice for cellular tissue body.

PRIOR ART REFERENCE

Patent Document

[Patent Document 1] JP-A-2006-122012

SUMMARY OF THE INVENTION

Problems to be Solved by the Invention

Objects of the present invention are to provide a method of recovering rare cells in which, when a cell suspension containing a large amount of various kinds of cells, such as blood, is spread in a flow path arranged on a microchamber chip, the loss of the cells can be reduced by improving the ratio of the total number of cells that can be retained in each microchamber with respect to the total number of the cells contained in the cell suspension (hereinafter, this ratio is also referred to as "cell recovery rate"); and to provide a method of recovering the rare cells.

Technical Solution

When a cell suspension is added to the microdevice for cellular tissue body disclosed in Patent Document 1 and left to stand for a prescribed time and a liquid is subsequently fed to the microdevice in a continuous and uniform manner at a low flow amount, the cells adhering to the outside of the cell holding chambers are not moved. On the other hand, at a high flow amount, the cells are not likely to be stored in the cell holding chambers, and the cells once stored in the cell holding chambers are not easily released therefrom.

The present inventors intensively studied the liquid feeding process to discover that the cell recovery rate is markedly improved by, after spreading cells contained in a cell suspension using a cell-spreading device, intermittently providing a moving force that moves the positions of the cells spread in a flow path arranged on a microchamber chip, thereby completing the present invention.

That is, in order to achieve one of the above-described objects, the method of recovering rare cells that reflects one aspect of the present invention is a method of recovering rare cells contained in a cell suspension into a microchamber(s) by introducing the cell suspension to a cell-spreading device in which a flow path is formed on a microchamber chip comprising the microchamber(s) capable of storing and retaining cells, the method comprising: the step (X) of spreading cells on the microchamber chip by allowing the cell suspension to flow in the flow path of the cell-spreading device; and the step (Y) of intermittently providing a moving force that moves the positions of the cells thus spread in the flow path on the microchamber chip.

Advantageous Effects of Invention

According to the present invention, even various kinds of cells contained in a cell suspension such as blood can be recovered into the microchamber(s) at an extremely high recovery rate, that is, almost all of the cells that are spread in the cell-spreading device comprising a flow path formed on the microchamber(s) can be stored and retained in the microchamber(s), so that the loss of rare cells that may exist in the cell suspension can be reduced.

BRIEF DESCRIPTION OF DRAWINGS

FIG. 3(A) shows the cell-spreading device in which the bottom surface of the flow path is formed by a microchamber chip 1. FIG. 3(B) shows the cell-spreading device in which the bottom surface of the flow path is formed by the microchamber chip 1 and a flow path-forming frame 2.

FIG. 4(A) shows a top view of the cell-spreading device, and FIG. 4(B) is a cross-sectional view of the cell-spreading device shown in FIG. 4(A), which is taken along the line A'-A'.

DESCRIPTION OF EMBODIMENTS

The method of recovering rare cells and the method of detecting rare cells according to the present invention will now be described in detail referring to FIGS. 1 to 8.

The method of recovering rare cells according to the present invention is a method of recovering rare cells that may be contained in a cell suspension from the cell suspension using a cell-spreading device, the method comprising the steps (X) and (Y) and, preferably, the step (W) and/or the step (Z).

It is preferred that the above-described moving force be a force that moves cells positioned outside the microchamber(s).

It is preferred that the method of recovering rare cells according to the present invention further comprise, before the step (X), the step (W) of wetting the surface of the microchamber chip by feeding thereto an aqueous solution having a surface tension lower than that of water.

In the step (X), it is preferred that cells be uniformly spread in the flow path on the microchamber chip by controlling the flow rate of the cell suspension introduced into the flow path.

In the step (Y), it is preferred that the moving force be intermittently provided such that the cells positioned outside the microchamber(s) are moved reciprocally.

In the step (Y), it is preferred that the moving force be intermittently provided by performing intermittent liquid feeding in which a cycle of feeding a liquid and stopping the feeding is repeated.

It is preferred that the method of recovering rare cells according to the present invention further comprise, after the step (Y), the step of removing some of the cells stored in layers in said microchamber(s) from the microchamber(s) by continuously feeding a liquid at a flow rate which is the same as or higher than the maximum flow rate of the above-described intermittent liquid feeding.

It is preferred that the rare cells be any one or more of circulating tumor cells [CTCs], circulating vascular endothelial cells [CECs] and circulating vascular endothelial precursor cells [CEPs].

It is preferred that the flow path be formed by arranging a flow path-forming frame integrally with the microchamber chip.

It is preferred that an inlet port and an outlet port be arranged on the flow path-forming frame, the inlet port and the outlet port being in communication with the flow path.

In order to achieve the other object described above, the method of detecting rare cells that reflects one aspect of the present invention comprises: recovering rare cells by the above-described method of recovering rare cells; and subsequently feeding a cell staining solution to the flow path of the microchamber(s) to perform cell staining and detection of the rare cells. It is noted here that the term "feeding" used herein encompasses continuous liquid feeding and intermittent liquid feeding.

A rare cell recovery system, comprising: a cell-spreading device in which a flow path is formed on a microchamber chip comprising a microchamber capable of storing and retaining cells; a liquid-feeding device which feeds a cell suspension to the flow path of the cell-spreading device; and a means for intermittently providing a moving force that moves the positions of cells spread on the microchamber chip, the rare cell recovering system carrying out the method according to any one of claims 1 to 11.

The above-described rare cell recovery system, further comprising an optical detection system capable of detecting rare cells stained with a cell staining solution, said rare cell recovery system carrying out the detection method according to claim 11.

<Cell-Spreading Device>

FIG. 3(A) shows one example of a cell-spreading device that can be used in the method of recovering rare cells according to the present invention.

As shown in FIG. 3(A), this cell-spreading device 10 comprises: a microchamber chip 1, on which microchamber 6s are formed; a flow path-forming frame 2, which is arranged integrally with the microchamber chip 1 such that a flow path 5 is formed on the microchamber 6s; an inlet port 3, which is arranged on the flow path-forming frame 2; an outlet port 4, which is arranged on the flow path-forming frame 2 for allowing a cell suspension introduced to the flow path 5 via the inlet port 3 to be discharged from the flow path 5; and the like.

<<Microchamber Chip>>

The microchamber chip 1, which is also referred to as "microchamber array [MCA]", comprises one or more microchamber 6s on the surface.

The "microchamber" refers to a recessed fine hole (microwell) that is capable of "storing" and "retaining" one or more cells and preferably has a bottom (that is, not a penetrating hole).

The term "retain" used herein refers to a condition in which feeding or the like of a staining solution or washing solution to the flow path of the microchamber chip for spreading of cells hardly causes the cells stored in a microchamber to be released therefrom.

It is preferred that the microchamber 6s have a diameter of 20 μm to 500 μm at the upper part of the opening. When the diameter is in this range of 20 μm to 500 μm, cells can be suitably stored and retained in the microchamber 6s.

It is preferred that the depth of the microchamber 6 be changed depending on the diameter of the microchamber 6, and the depth of the chamber can be determined as appropriate in accordance with the number of cells desired to be stored in each microchamber. Specifically, it is preferred that the depth of the chamber be determined such that the chamber can store about 10 to 15 cells, and the depth of the microchamber 6 is typically 20 μm to 500 μm.

Figure 3:
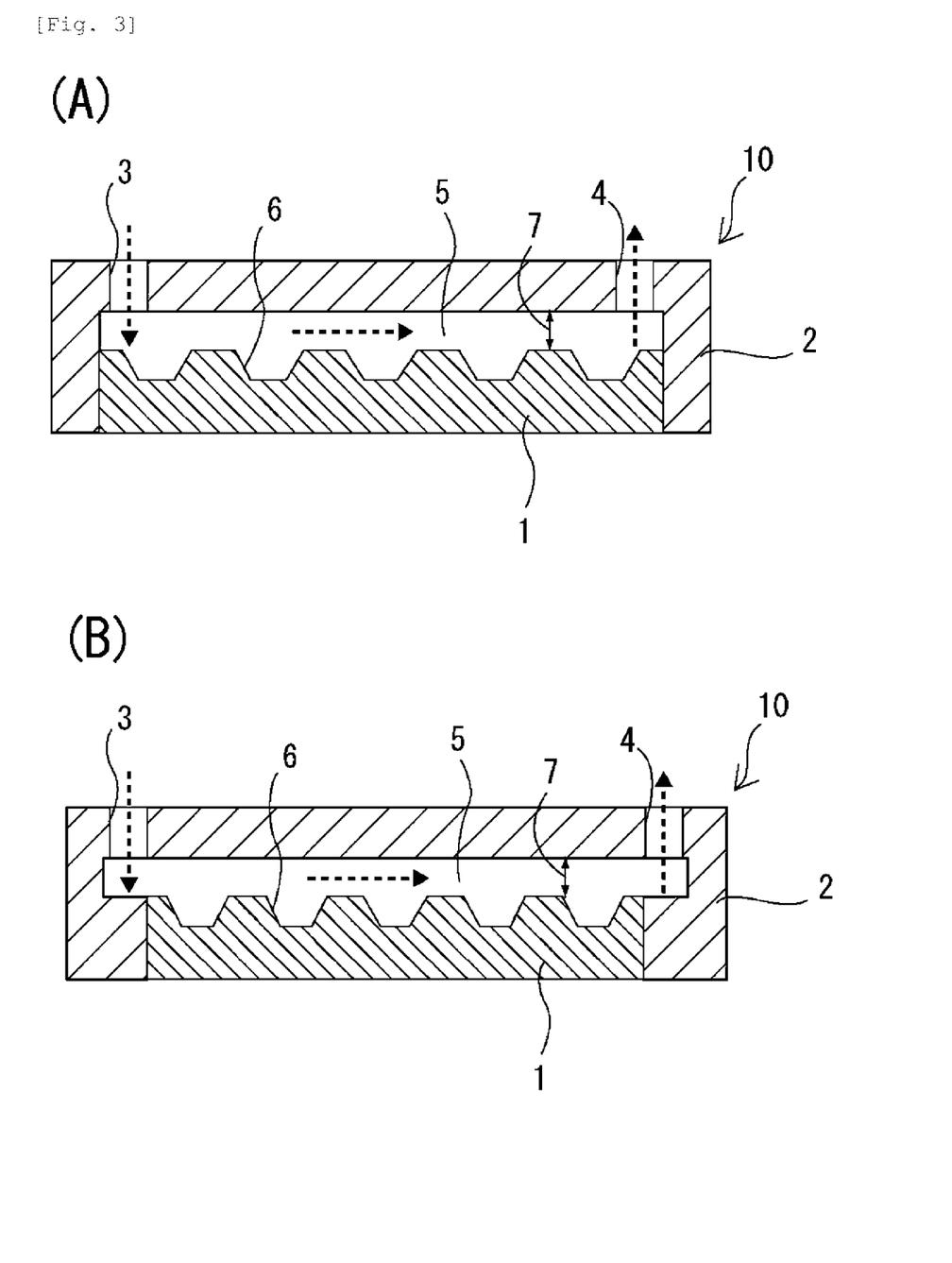
FIG. 3 schematically shows cross sections taken along the direction of the flow path of the cell-spreading device. The dashed arrow represents the direction of liquid flow in the flow path.
Figure 4:
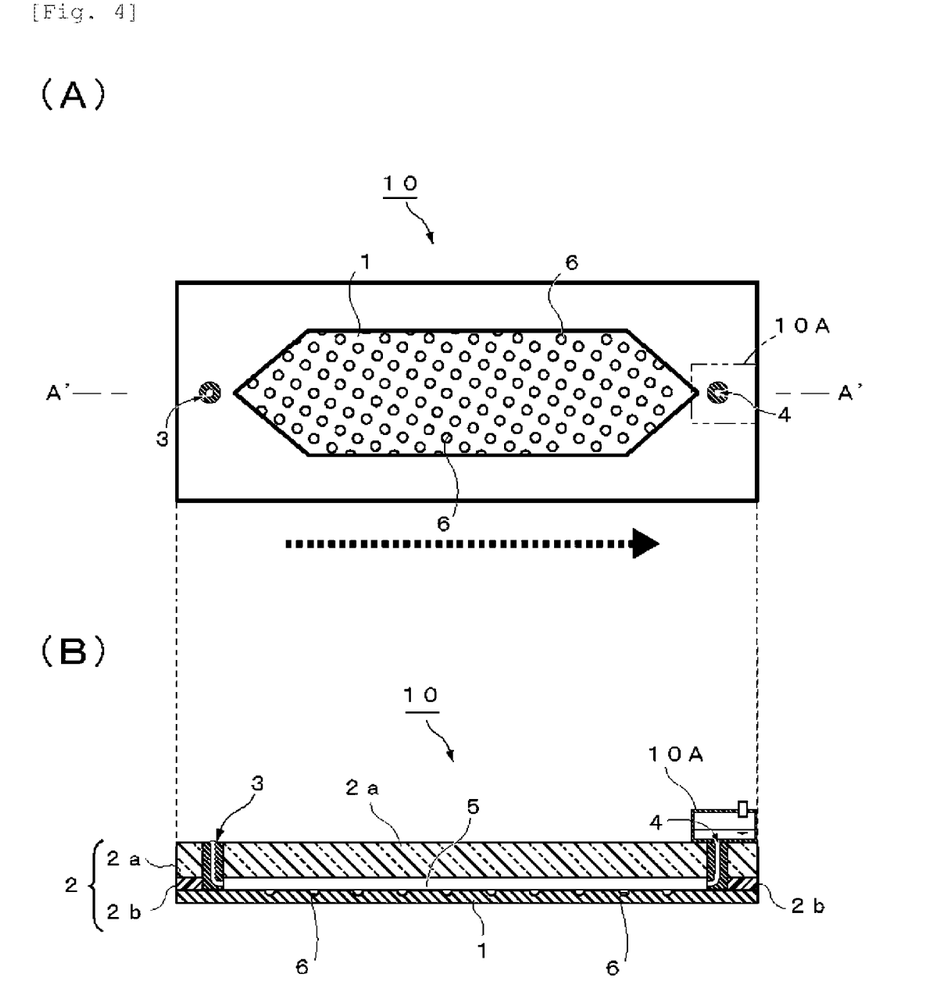
FIG. 4 schematically shows a concrete example of the cell-spreading device.
Figure 5:
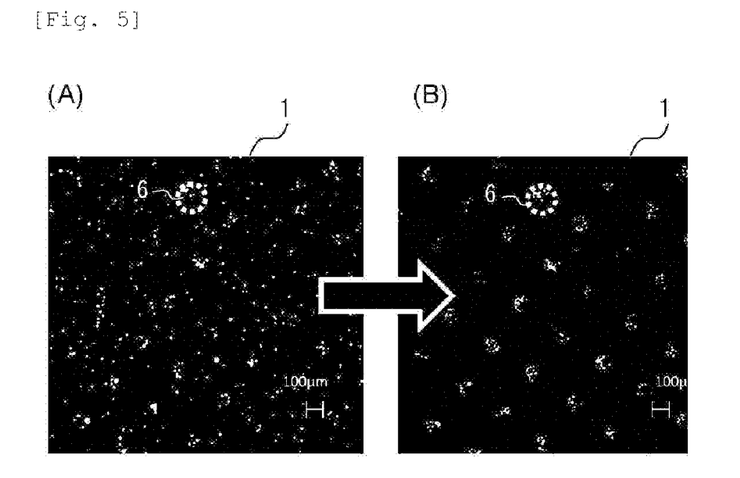
FIG. 5(A) is an enlarged image of the microchamber chip surface after the step (X) of Example 1.
FIG. 5(B) is an enlarged image of the microchamber chip surface after the step (Y) of Example 1.

In FIG. 3, the microchamber 6s have an inverted conical shape with a flat bottom (the longitudinal cross section is trapezoidal); however, the shape of the microchamber 6s is not restricted thereto, and it may be, for example, cylindrical, inverted hemispheric, inverted pyramidal (inverted polygonal pyramidal shape such as an inverted quadrangular pyramid shape or an inverted hexagonal pyramid shape) or cuboidal. The bottom of the microchamber 6 is typically flat; however, it may be curved as well.

By increasing the adhesive strength between the bottom of the microchamber 6s and the cells, the ratio at which cells can be surely retained in the microchamber 6s is increased. Therefore, as a method of increasing the cell-adhering strength of the bottom of the microchamber 6s, it is more preferred to subject the bottom of the microchamber 6s to, for example, a UV-ozone treatment in which UV is irradiated in the air, an oxygen-plasma treatment in which a plasma is irradiated in an oxygen atmosphere, or a coating treatment in which the bottom of the microchamber 6s is coated with a ligand (antibody) specifically binding with a cell of interest.

As the material of the microchamber chip 1, the same material as that of a conventionally known microplate or the like can be used, and examples thereof include polymers such as polystyrene, polyethylene, polypropylene, polyamide, polycarbonate, polydimethylsiloxane [PDMS], polymethyl methacrylate [PMMA] and cyclic olefin copolymers [COCs]. The microchamber chip 1 may be composed of a combination of plural materials, such as a molded polymer laminated with a substrate made of a metal, glass, quartz glass or the like.

As a method of producing the microchamber chip 1, a method of molding the above material using a mold having a protrusion corresponding to the shape of the microchamber 6 on the surface of the mold base material or a method of forming the microchamber by direct processing (e.g., microprocessing by lithography, drilling, or LIGA process) of a substrate made of the above-described polymer, metal, glass or the like can be employed; however, from the productivity standpoint, a molding method using a mold is preferred.

<<Surface Treatment>>

As required, the microchamber chip 1 can be subjected to a surface treatment. Examples of the surface treatment include, but not limited to, a plasma treatment (e.g., an oxygen-plasma treatment), a corona discharge treatment, and a coating treatment with a hydrophilic polymer, a protein, a lipid or the like.

In cases where a surface treatment is performed, the microchamber chip 1 for spreading cells is subjected to a surface treatment that makes even the inner wall surfaces of the microchamber 6s non-adhesive with cells. In this surface treatment, a blocking agent is used. The "blocking agent" refers to a substance which coats the flow path 5 formed by the inner surfaces of the microchamber 1 and flow path-forming frame 2 and thereby inhibits non-specific adsorption of cells thereto.

By the surface treatment, cells are made more likely to be accumulated on the bottom surfaces of the microchamber 6s without adsorbing to the inner wall, so that cells can be easily observed in a bright field under a microscope.

Examples of the blocking agent include hydrophilic macromolecules such as caseins, skim milk, albumins (including bovine serum albumin [BSA]) and polyethylene glycol; phospholipids; and low-molecular-weight compounds such as ethylene diamine and acetonitrile. These blocking agents may be used individually, or two or more thereof may be used in combination.

A blocking treatment solution is prepared by diluting the blocking agent with an appropriate solvent, and this solvent is selected in accordance with the blocking agent. For example, in cases where BSA is used as the blocking agent, it is preferred to select the same solvent as the one which is used for suspending the cells to be spread and is compatible with biologically relevant substances. Specifically, phosphate-buffered physiological saline [PBS], HEPES, MEM, RPMI, phosphate buffer or the like can be used.

<<Flow Path>>

On the microchamber chip of the cell-spreading device, a flow path mainly used for allowing a cell suspension to flow therethrough is formed.

For instance, one example of the flow path is shown in FIG. 3(A); however, the flow path is not restricted thereto as long as it is capable of allowing a cell suspension to flow on the microchamber chip 1.

In the example shown in FIG. 3(A), the flow path 5 is formed in such a manner that its bottom surface is constituted by the surface of the microchamber chip 1, excluding those parts of the microchamber 6s, and the side surface and the ceiling part are constituted by the inner surface of the flow path-forming frame 2 arranged integrally with the microchamber chip 1.

This flow path 5 is in communication with the inlet port 3 and outlet port 4 of the flow path-forming frame 2 such that the cell suspension introduced to the flow path 5 via the inlet port 3 flows through the flow path 5 in the direction represented by the dashed arrow and is then discharged from the outlet port 4.

Alternatively, for example, as in another example of the flow path shown in FIG. 3(B), the bottom surface of the flow path may be formed by those parts of the surface of the microchamber chip 1 other than the parts of the microchamber 6s and a part of the inner surface of the flow path-forming frame 2.

However, in this case, if the bottom surface below the inlet port 3 or outlet port 4 to which the cell suspension flows down has a part where the microchamber 6 is not formed, retention, adhesion or the like of cells to this part may prevent the cells from being stored into the microchamber 6s, which leads to loss of the cells.

In order to prevent this, it is desired to replace such a problematic bottom part with a part of the microchamber chip 1, or to form the inlet port 3 and the like to prevent the cell suspension from flowing down to the problematic bottom part, so that the flow path is not formed by a member other than the microchamber chip 1.

From the standpoint of the easiness of observation and maintenance, it is preferred that the microchamber chip 1 and the flow path-forming frame 2 be constituted in such a manner that they can be attached and detached from each other by a means such as engagement, screw fixation or adhesion (not shown).

Further, it is also preferred that the microchamber chip 1 and the flow path-forming frame 2 be constituted in such a manner that, after the flow path 5 is formed by attachment or the like thereof, only the ceiling part (flow path top plate) can be detached from the flow path-forming frame 2, leaving only the side surface parts.

The height 7 of the flow path 5 (see FIG. 3(A) and FIG. 3(B)), that is, the distance between the part of the surface of the microchamber chip 1 other than those parts of the microchamber 6s and the ceiling part (hereinafter, also referred to as "the ceiling height"), is preferably 50 μm to 500 μm.

When the ceiling height is in a range of 50 μm to 500 μm, the cells adhering to those parts of the surface of the microchamber chip 1 other than the parts of the microchamber 6s can be easily moved by the force of liquid flow. In addition, the time required for the cells to precipitate onto the surface of the microchamber chip 1 can be shortened. Moreover, clogging and the like of the flow path caused by the cells are less likely to occur, and the cells can thus be spread smoothly.

As the material of the flow path-forming frame 2, for example, the same as that of the microchamber chip 1 is preferably used.

Here, in the same manner as the microchamber chip 1, the flow path-forming frame 2 may also be subjected to the above-described surface treatment (e.g., an electrical treatment such as plasma treatment or corona discharge treatment, or a coating treatment with such a hydrophilic polymer, protein, lipid or the like that preferably binds with contaminants other than the rare cells of interest).

Alternatively, for example, as shown in FIG. 4(B), the flow path 5 can be formed by constituting the flow path-forming frame 2 using a flow path top plate 2a and a double-sided adhesive silicon sheet, that is, a flow path seal 2b, and holding the flow path seal 2b using its adhesiveness between the flow path top plate 2a and the microchamber chip 1. It is noted here that the symbol represents an auxiliary frame.

In such a constitution that an elastic silicon sheet is held by a fixation means, by controlling the holding strength, the dimensions of the flow path such as the ceiling height and the flow path volume can be adjusted, so that the pressure of a liquid fed into the flow path, the flow rate and, in turn, the ease of spreading cells and the like can also be adjusted.

Further, as shown in FIG. 4(B), a reservoir 10A may be arranged in connection with the outlet port 4 of the flow path 5. This reservoir 10A has a volume of, for example, about 500 μL, and the cell suspension introduced via the inlet port 3 is discharged from the outlet port 4 and temporarily pooled in the reservoir 10A.

<Cell Suspension>

The cell suspension is, for example, a blood, lymphatic fluid, interstitial fluid or coelomic fluid of a human or the like that potentially contains rare cells, and it may be diluted with a diluent as appropriate. Further, the cell suspension is not restricted to one originated from a living body, and it may be a cell suspension prepared by artificially suspending cells for testing, research or the like. Particularly, for the recovery and detection of rare cells such as CTCs, it is preferred to apply a cell suspension obtained by separating erythrocytes from a blood sample.

Examples of the rare cells include cancer cells. Particularly, when the cell suspension is a blood or blood-derived sample, the rare cells may be any one or more of CTCs [circulating tumor cells or circulating cancer cells], CECs [circulating vascular endothelial cells] and CEPs [circulating vascular endothelial precursor cells].

The various cells contained in such a cell suspension preferably have a diameter of 10 to 100 μm, and the diameter is required to be at least smaller than that of the microchamber.

<Step (W)>

The step (W) is a step of, before the below-described steps (X) and (Y), wetting the surface of the microchamber chip by feeding thereto an aqueous solution having a surface tension lower than that of water.

The aqueous solution having a surface tension lower than that of water is not particularly restricted as long as its surface tension is lower than that of water.

The lower the surface tension of the aqueous solution to be fed, the more can the inside of the microchamber 6s be wetted; therefore, under a temperature environment where the aqueous solution is fed, the surface tension γ (mN/m) of the aqueous solution to be fed is in a range of usually $10 \leq \gamma \leq 60$, preferably $10 \leq \gamma \leq 40$, more preferably $10 \leq \gamma \leq 35$, still more preferably $10 \leq \gamma \leq 30$, yet still more preferably $10 \leq \gamma \leq 25$.

Examples of the aqueous solution having a surface tension lower than that of water include aqueous solutions including an alcohol such as ethanol, methanol or isopropyl alcohol; and aqueous solutions containing 0.01 to 1% (w/v) of a surfactant such as TWEEN (registered trademark) 20, TRITON (registered trademark) X or SDS. For example, the surface tension of ethanol (aqueous solution) at 20° C. is 22.4 at a concentration of 100 wt %, 26.0 at a concentration of 70 wt %, and 47.9 at a concentration of 10 wt %.

By feeding the above-described aqueous solution to the flow path 5 of the cell-spreading device 10, not only the outside but also the inside of the microchamber 6s can be wetted (see FIG. 3(A) or (B)).

It is preferred that the flow path 5 be subsequently filled with a physiological saline such as PBS [phosphate-buffered physiological saline] (preferably, the same solvent as that of the cell suspension used in the step (X)).

<Step (X)>

The step (X) is a step of introducing the cell suspension to the flow path to spread (preferably uniformly) cells in the flow path on the microchamber chip.

Preferably, in cases where the cell suspension is continuously and uniformly fed via the inlet port 3 and the flow path has been previously filled with a physiological saline in the step (W), the flow path 5 is filled with the cell suspension in such a manner that the cell suspension replaces the physiological saline. In this process, the physiological saline is discharged from the outlet port 4 simultaneously with the introduction of the cell suspension via the inlet port 3 (see FIG. 3(A) and FIG. 3(B)).

Figure 2:
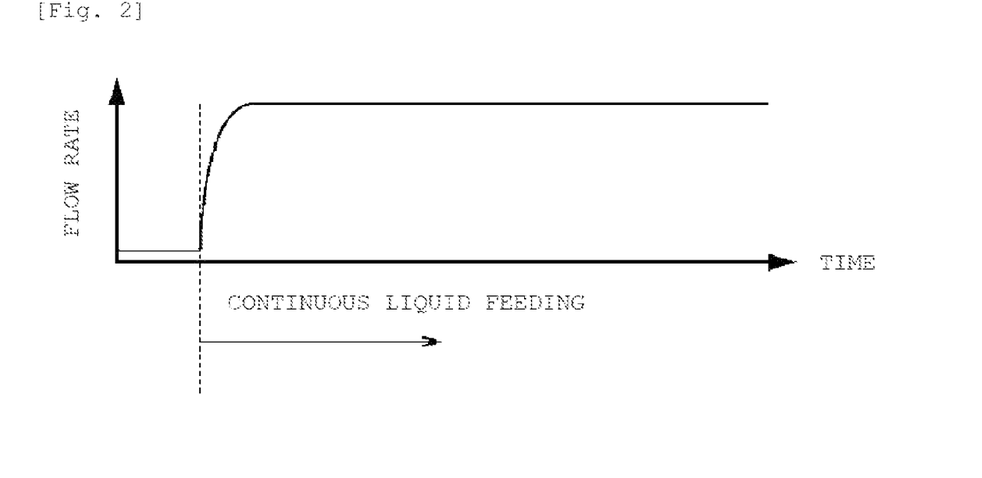
FIG. 2 is a graph plotting the change with time in the flow rate inside the flow path when a liquid is continuously fed to the flow path of the cell-spreading device.

The phrase "continuously and uniformly fed" (hereinafter, also referred to as "continuous feeding") used herein refers to such feeding in which, as shown in FIG. 2, the flow rate is maintained constant in the flow path.

As for the flow rate of the cell suspension introduced to the flow path, the cells become less likely to remain in the microchamber 6 near the inlet port 3 of the cell-spreading device 10 in proportion to the increase in the flow rate; therefore, the higher the flow rate is set, the more uniformly spread the cells are in the longitudinal direction of the microchamber 6.

Depending on the balance with the dimensions and the like of the flow path, however, if the flow rate is set unnecessarily high, the cells conversely become less likely to be spread in the transverse direction of the microchamber chip. Therefore, it is required to appropriately set the flow rate at a level suitable for the cell-spreading device such that the cells are spread in a well-balanced and uniform manner in both the longitudinal and transverse directions.

In the cell-spreading device described in Examples below, if the flow rate of the cell suspension introduced to the flow path were set to be 10 mL/min or higher, the cells would have been unlikely to be spread in the transverse direction of the microchamber chip and the cells would consequently have been not uniformly spread; therefore, the flow rate was set at about 1 mL/min to be in a range of not higher than 10 mL/min.

After the introduction of the cell suspension, it is preferred that the cells contained therein be allowed to precipitate by leaving the cell suspension to stand for a certain period of time (for example, 1 to 15 minutes). Here, for example, as shown in FIG. 5(A), some of the cells are stored in the microchamber 6s, while some of other cells adhere to the parts of the surface of the microchamber chip 1 other than those parts of the microchamber 6s.

When the cells are uniformly spread in the flow path on the microchamber chip 1, more cells can be recovered in the microchambers by the below-described intermittent liquid feeding performed in the step (Y).

As a result, the time required for the cell recovery rate to reach a prescribed level in the step (Y) can be shortened, that is, the cells become more likely to be stored in the microchamber 6s with a less number of intermittent liquid feeding operations, which is preferred.

<Step (Y)>

The step (Y) is a step of storing the cells existing in the flow path into the microchambers by intermittently imparting the cells spread in the flow path on the microchamber chip with a moving force by an operation such as intermittent liquid feeding and thereby moving the positions of the cells.

This moving force is preferably a force enough to move primarily the cells positioned in the flow path outside of the microchambers.

<<Intermittent Liquid Feeding>>

Figure 1:
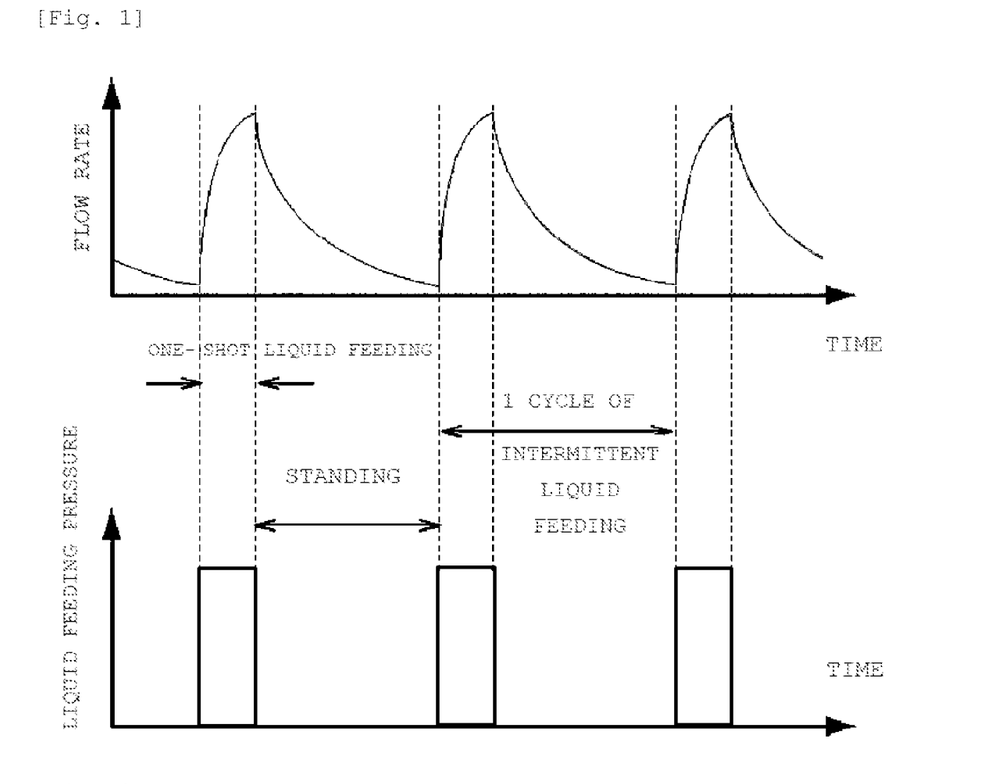
FIG. 1 is a graph showing the changes with time in the liquid feeding pressure and the flow rate inside the flow path when "intermittent liquid feeding" is performed to the flow path of the cell-spreading device in the step (Y).

As shown in FIG. 1, the "intermittent liquid feeding" consists of: a relatively short period of "one-shot liquid feeding", which is performed to move the cells spread in the flow path on the microchamber chip, particularly the cells existing on the parts of the surface of the microchamber chip other than those parts of the microchambers; and a relatively long "standing" time for allowing the cells to substantially precipitate on the surface of the microchamber chip, basically without moving the cells in the direction of the liquid feeding.

The period from the start of the "one-shot liquid feeding" until the end of the "standing" time, that is, the period between the start of the "one-shot liquid feeding" and the next "one-shot liquid feeding", is defined as 1 cycle of the intermittent liquid feeding.

The "one-shot liquid feeding" is performed when a liquid feed-driving device feeds a liquid in such a manner that a prescribed feeding pressure is generated in the flow path for a prescribed time and at least some of the cells in the flow path are moved to directly above the microchambers. The pressure and duration of the one-shot liquid feeding can be set by carrying out the liquid feeding while verifying the amount of the cell movement under a microscope or the like. It is preferred that, by the one-shot liquid feeding, the cells in the flow path be moved by about the diameter of the microchambers.

The "standing" is performed when the liquid feed-driving device does not generate any feeding pressure (that is, when the device is in a non-operating state). The "standing" period may include a condition in which the flow rate is not zero due to the inertia of the feeding pressure generated immediately therebefore.

By this one-shot liquid feeding, in the flow path, not only a high-pressure condition is momentarily created but also a condition in which the flow rate is nearly constant in the direction perpendicular to the direction of the flow path from the center of the flow path to the periphery of the flow path on both sides is created, so that the cells adhering to, for example, those parts of the surface of the microchamber chip other than the parts of the microchambers are also made likely to be moved. By the subsequent "standing" process, at least some of the moved cells are stored in the microchambers.

In the one-shot liquid feeding, a solution which does not adversely affect the recovery and the detection of rare cells is used. Preferably, a prescribed amount of a physiological saline (for example, the same buffer as that of the cell suspension used in the step (X)) is fed to the flow path.

The amount of such a liquid to be fed is preferably set at, for example, $\frac{1}{100}$ to $\frac{1}{2}$ or so of the volume of the cell suspension introduced to the flow path.

Further, when the flow path has a cross section of 1 to 1,000 mm$^2$, it is preferred to adjust the amount of the liquid to be fed per unit time to be 1 to 1,000 µL/sec (this flow amount per second corresponds to a flow rate of 1 mm/sec or less).

Specifically, for example, in cases where a cell-spreading device in which a flow path (width: 15 mm, height: 100 µm) is formed on a microchamber chip having microchambers (diameter: 100 µm, depth: 50 µm) on the surface is used, since the flow path has a cross section of 1.5 mm$^2$, it is preferred to adjust the flow amount to be 1,500 µL/sec or less.

After the one-shot liquid feeding, the cell-spreading device is left to stand for a prescribed time (for example, 1 to 30 seconds). Specifically, the cell-spreading device is subjected to this standing process for, for example, 3 to 5 seconds.

One cycle of the intermittent liquid feeding, which is the period from the one-shot liquid feeding to the end of the standing process, is repeated preferably not less than twice, more preferably not less than 10 times, still more preferably not less than 60 times. By performing the one-shot liquid feeding once, cells are usually moved by about 50 µm.

In cases where plural cycles of the intermittent liquid feeding are performed, the conditions such as the amount of the one-shot liquid feeding and the standing time may be the same between cycles or different from cycle to cycle.

Further, the intermittent liquid feeding may be performed only through the inlet port; however, it may also be performed alternately through the inlet port and the outlet port.

Specifically, the intermittent liquid feeding may be made to the flow path through the inlet port once or more times and then through the outlet port once or more times.

By performing the intermittent liquid feeding alternately through both the inlet port and the outlet port, the cells that have passed by the microchambers without being stored therein can be moved reciprocally in the opposite directions, so that such cells can be stored into the microchambers and the cell recovery rate can thereby be improved.

The number of the intermittent liquid feeding may be an integer close to a value obtained by dividing the pitch length between the microchambers by the distance of the cell movement made by each one-shot liquid feeding.

In this manner, the cells can be recovered in the microchambers while maintaining as much as possible the density of the cells uniformly spread on the microchamber surfaces after the introduction of the cell suspension, and this makes it unlikely that the number of the stored cells varies among the microchambers. Consequently, the likelihood that one of the microchambers is saturated with cells is also reduced.

Further, taking a series of the intermittent liquid feeding performed alternately in the above-described manner as one set, such a set of intermittent liquid feeding may be performed repeatedly. By this, the cell recovery rate can be further improved.

It should be noted here that the intermittent liquid feeding is not restricted to the above-described intermittent liquid feeding performed via the inlet port and/or the outlet port, as long as it is capable of moving the cells in the flow path in a reciprocating manner.

<<Method Other than Intermittent Liquid Feeding>>

The method of providing a moving force that moves the positions of the cells spread in the flow path is not restricted to the above-described intermittent liquid feeding, as long as it is capable of intermittently providing a moving force that moves the positions of the cells spread in the flow path on the microchamber chip.

For example, such a moving force can be imparted to the cells spread in the flow path by intermittently force-feeding, instead of a physiological saline, a gas that does not adversely affect cells such as nitrogen gas or air into the flow path and thereby moving the cell suspension in the flow path. In order to prevent the cell suspension in the flow path from excessively moving and creating a condition in which the cell suspension is absent from a part of the flow path, it is preferred that the force-feeding of such a gas be performed alternately via the inlet port and the outlet port.

By this constitution, not only a moving force can be intermittently imparted to the cells spread in the flow path but also, because of no addition of physiological saline or the like, unnecessary dilution of the cell suspension can be prevented, so that a reduction in the cell recovery rate can be inhibited.

Apart from this, a moving force can also be intermittently imparted to the cells spread in the flow path by centrifuging the microchamber chip such that a centrifugal force is applied in the direction from the inlet port to the outlet port of the flow path. Here, the moving direction of the cell suspension may also be reversed by rotating the microchamber chip by 180° and thereby reversing the direction of the applied centrifugal force.

The centrifugation is preferably performed at such a low speed that does not excessively move the cells (for example, 1 to 100 r.p.m. or so); however, the centrifugation speed is also required to be adjusted in accordance with the cell type and the shape of the device. By this constitution, as described above, dilution of the cell suspension by an addition of physiological saline or the like and a reduction in the recovery rate caused thereby can be prevented.

Furthermore, a moving force can also be imparted to the cells in the flow path by intermittently tilting the microchamber chip using a shaker or the like and thereby moving the cell suspension, or by intermittently applying vibration to the microchamber chip.

<Step (Z)>

The step (Z) is a step of, after the above-described step (Y), removing some of the cells stored in layers in the microchamber(s) from said microchamber(s) by continuously feeding a liquid at a flow rate which is the same as or higher than the maximum flow rate of the above-described intermittent liquid feeding.

By performing the step (Z), the cells in the microchambers are made into a single layer, so that a condition where the cells can be easily stained and observed is created.

After the cells are spread, by performing the intermittent liquid feeding and the continuous liquid feeding in combination, the cells stored and retained in each microchamber can be made into a single layer, which is preferred for observation of the cells.

When an excess number of cells are stored and retained in the microchamber $6s$, assuming that the cells are grouped into a layer (first layer) composed of cells adhering to the bottom surface of each microchamber 6 and a layer (second layer) composed of cells adhering to this cell layer, normally, the adhesive strength between the first layer cells and the second layer cells is weaker than that between the bottom surfaces of the microchamber $6s$ and the first layer cells. Therefore, when a liquid is continuously fed at a flow rate which is the same as or higher than the maximum flow rate of the above-described intermittent liquid feeding, the second layer cells are likely to be removed out of the microchamber 6.

The method of detecting rare cells according to the present invention comprises the below-described staining step and detection step in addition to the above-described recovery of rare cells.

<<Staining Step>>

The staining step is a step of staining the rare cells retained in the microchambers with a staining solution capable of staining only specific rare cells of interest (for example, a solution of an antibody labeled with a fluorescent dye).

(Circulating Tumor Cell [CTC])

As for whether or not the cells are circulating tumor cells [CTCs], cells that are positive for nuclear staining and negative for CD45 (non-leukocytes) can be judged as CTCs. This nuclear staining can be performed using, for example, a non-cytotoxic neutral red solution, and the presence or absence of CD45 can be determined by, for example, an antigen-antibody reaction using a fluorescently labeled anti-CD45 antibody. By performing these stainings on the cells stored in the microchambers, it can be judged which of these cells in the microchambers are CTCs.

(Circulating Vascular Endothelial Cell [CEC])

Further, as for whether or not the cells are circulating vascular endothelial cells [CECs], for example, expression of an endothelial cell marker (CD31 or CD51/61) can be judged by staining the cells with an anti-CD31 antibody or anti-CD51/61 antibody that is labeled with a fluorescent substance or the like. In this case, for whether or not the thus determined CECs are also tumor cells, which of these cells are tumorous endothelial cells can be judged by staining the cells stored in the microchambers with anti-human CD146 labeled with a fluorescent substance or the like, which specifically reacts with CD146 expressed in tumorized endothelial cells.

(Circulating Vascular Endothelial Precursor Cell [CEP])

For example, for the cell populations in the respective microchambers, which cells thereof are circulating vascular endothelial precursor cells [CEPs] can be determined by: performing a conventional ALDH activity measurement (cellular ALDH (enzyme)+BAAA (substrate, Bodipy-aminoacetaldehyde)→(BAA-(Bodipy-aminoacetate, fluorescent emission)); specifying a cell population(s) containing circulating vascular endothelial precursor cells [CEPs] that show higher ALDH activity using the thus measured ALDH activity as an index; and further subjecting the thus specified cell population(s) to ALDH activity measurement in the same manner.

In the staining step, for example, as shown in FIGS. 3(A) and 3(B), a staining solution capable of staining only specific rare cells of interest (for example, a solution of an antibody labeled with a fluorescent dye) is introduced via the inlet port 3 and allowed to react with the cells under specific conditions, and the staining solution is subsequently discharged from the outlet port 4. Further, the washing step, in which a washing solution is introduced via the inlet port 3 to wash the cells as well as inside the flow path 5 and the washing solution is subsequently discharged from the outlet port 4, is performed at least once.

While the cells that are retained in the microchamber 6s are unlikely to be discharged from the outlet port 4 along with the staining solution and the washing solution, those cells adhering to the parts of the surface of the microchamber chip 1 other than the parts of the microchamber 6s are likely to be discharged from the outlet port 4 along with the staining solution and the washing solution.

That is, after the cells are spread, in the step of staining rare cells and subsequent washing step that are performed for detection of the rare cells, those cells remaining on the parts of the surface of the microchamber chip other than the parts of the microchambers may be discharged from the outlet port along with the staining solution and the washing solution; however, since those cells that are stored and retained in the microchambers remain retained in the microchambers even after being subjected to the staining step and the washing step, hardly any of these cells are discharged from the outlet port. In order to strengthen the retention of the cells in the microchambers, it is more preferred to immobilize a ligand specifically binding with the cells of interest onto the bottom of the microchambers.

<<Detection Step>>

The detection step is a step of detecting the rare cells that are stained in the staining step and retained in the microchambers by observation and/or the use of a detection instrument or the like.

The rare cells retained and stained in the microchamber 6s can be subjected to observation, detection and the like under a microscope. It is preferred that the rare cells retained in the microchambers be detected in a monolayer state attained by the step (Z). Further, separation of the rare cells can be done by picking up only the rare cells using a cell-holding glass micropipette or the like from the microchambers containing the cells stained in the staining step.

<Rare Cell Recovery System>

Figure 8:
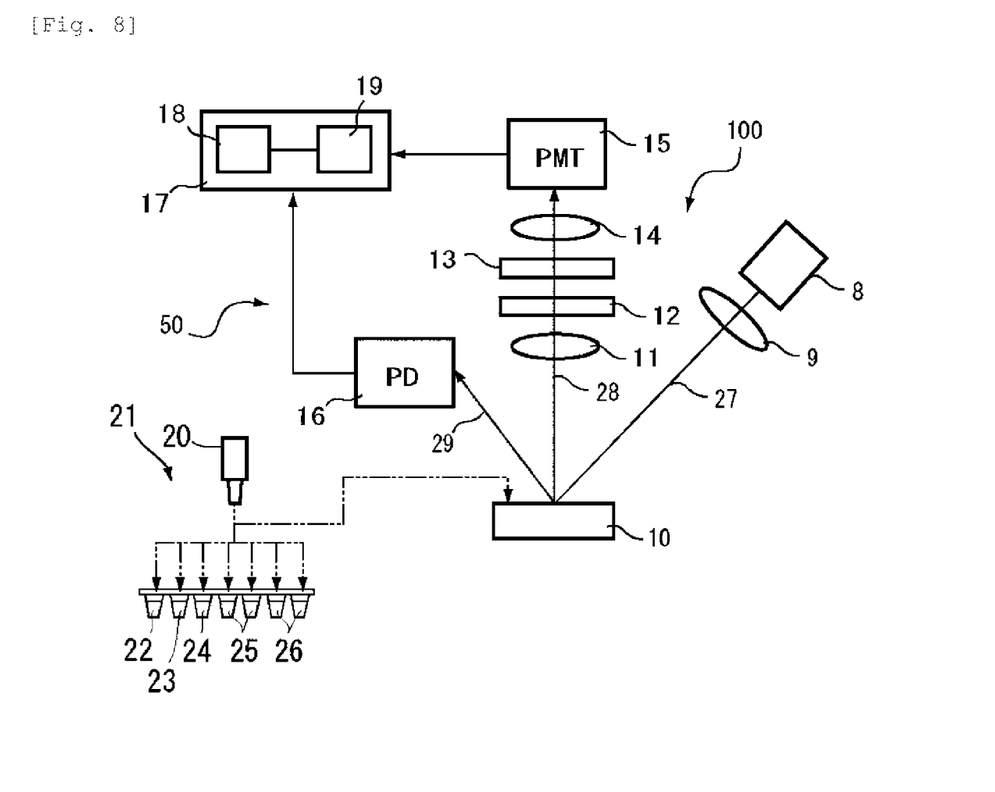
FIG. 8 shows a rare cell recovery system according to a preferred example of the present invention.

As shown in FIG. 8, a rare cell recovery system 100, which is a preferred example of the present invention, comprises: the above-described cell-spreading device 10; a liquid-feeding device 20, which comprises a pump capable of feeding a liquid to the flow path 5 of the cell-spreading device 10; a control means 17, which controls the operations of the respective members including liquid feeding and the like performed by the liquid-feeding device 20; and the like. More preferably, the rare cell recovery system 100 further comprises an optical detection system 50, which is used for detection of the rare cells recovered in the microchamber 6s of the cell-spreading device 10.

The control means 17 is an ordinary personal computer or the like and, in the example shown in FIG. 8, the control means 17 comprises a rare cell-specifying section 18, a memory medium 19 and the like. The memory medium 19 stores a program which controls the liquid-feeding device 20 for carrying out the steps (X), (Y) and (Z) in this order. In addition, the memory medium 19 also optionally stores a program for carrying out the step (W) before the step (X) and/or a program for carrying out the staining step and the detection step after the step (Z).

Furthermore, the control means 17 controls the liquid-feeding device 20 to collect the solutions stored in the liquid-feeding station 21 (a cell suspension sample 22, a washing solution 25, a staining solution (labeled-antibody solution) 24 and the like) and to feed these solutions (continuous liquid feeding or intermittent liquid feeding) to the flow path 6. In the intermittent liquid feeding, this control means 17 functions as a means for moving the positions of the cells spread on the microchamber chip.

In cases where, after the recovery of rare cells in the microchamber 6s, the above-described detection step is performed using the optical detection system 50 of the rare cell recovery system 100, the detection step is performed as follows. First, in a condition where cells are present in the microchamber 6s of the cell-spreading device 10, by the control of the control means 17, a light source 8 irradiates the microchamber 6s with an excitation light 27, which is reflected by the microchamber 6s and the flow path 5 of the cell-spreading device 10 to generate a reflected light 29 and, in some cases, fluorescence 28. It is noted here that the excitation light 27 has a wavelength capable of exciting the above-described fluorescent dye.

A chamber detection section 16, which is arranged at a prescribed light-receiving position, receives the reflected light 29 and, based on the intensity thereof, determines whether the excitation light 27 is irradiated at the position of any of the microchamber 6s or at the position of the flow path 5. Meanwhile, above the cell-spreading device 10, a condenser lens 11, an emission filter 12, a pinhole member 13, a condenser lens 14 and a PMT (photomultiplier tube) are arranged on the same axis in the order mentioned from the lower side. By the irradiation with the excitation light 27, the fluorescence 28 is emitted by the fluorescent label binding to the rare cells in the microchamber 6s and then guided to the rare cell detection section 15, which detects the fluorescence signals of the rare cells. It is noted here that this detection may also be performed by using a fluorescent microscope instead of the optical detection system. The control means 17 determines the presence/absence and the positions of the rare cells based on the intensity of the fluorescence 28 and controls the pump of the liquid feeding device 20 to pick up the rare cells.

As another example of the rare cell recovery system 100, in addition to the constitution of the rare cell recovery system 100, a shaker which is controlled by the control means 17 to intermittently provide a moving force that moves the positions of the cells spread on the microchamber chip in the above-described manner may also be arranged. Separately from this, a centrifugation apparatus, which comprises a holding means capable of holding the microchamber chip and is controlled by the control means 17 to intermittently applying a centrifugal force to the cell-spreading device 10 while holding one end thereof, thereby intermittently providing a moving force that moves the positions of the cells spread on the microchamber chip in the above-described manner, may also be arranged. Furthermore, for example, in such a case where the positions of the microchambers 6s on the cell-spreading device 10 had been put into the memory in advance to control the position of the cell-spreading device 10 or a case where a mark or the like of a reference position is placed on the cell-spreading device 10, it is not necessary to particularly detect the positions of the microchamber 6s and the chamber detection section 16 can be omitted for the controlling of the position of the cell-spreading device 10 and the like.

EXAMPLES

The present invention will now be described in more detail byway of examples thereof; however, the present invention is not restricted thereto.

Example 1

As a microchamber chip, a chip on which microchambers of 100 μm in diameter and 50 μm in depth were arranged in a lattice form (the pitch, which is the distance between the bottom centers of adjacent microchambers, was 210 μm) was used. This microchamber chip was made of polystyrene and had a bottom-flat inverted conical shape.

On the microchamber chip surface on which the microchambers were formed, a polystyrene-made flow path-forming frame was arranged such that a flow path of 15 mm in length, 26 mm in width and 100 μm in height was formed, and the microchamber chip and the flow path-forming frame were integrated with each other. The flow path of the thus obtained cell-spreading device had a cross-section of 1.5 mm² and a volume of 39 mm³ (=39 μL). As a liquid-feeding device, KDS200 dual syringe pump (manufactured by KD Scientific Inc.) was used.

On the flow path-forming frame, an inlet port and an outlet port were each formed in an integrated manner, which inlet port and outlet port were in communication with each other via the flow path.

As the step (W), after feeding 100 μL of 70% aqueous ethanol solution at a flow amount of 1 mL/min (flow rate=11.11 μm/sec), 200 μL of PBS was fed via the inlet port 3 of the cell-spreading device 10 at a flow amount of 1 mL/min to remove air bubbles from the microchambers.

As the step (X), 100 μL of a cell suspension prepared by suspending Jurkat cells fixed with 0.4% formaldehyde in PBS (1×10⁶ cells/mL) was continuously fed at a flow amount of 0.1 mL/min (flow rate=1.11 μm/sec) to spread the cells on the surface of the microchamber chip. FIG. 5(A) shows an enlarged image of the microchamber chip surface which was taken after leaving the microchamber chip for 5 minutes. The white dots represent the cells, which were dispersed and precipitated both inside and outside the microchambers.

As the step (Y), intermittent liquid feeding, which consisted of one-shot feeding of 0.1 μL of PBS to the flow path at a flow amount of 0.1 mL/min and subsequent 5-minute standing, was continuously performed 10 times. FIG. 5(B) shows an enlarged image of the microchamber surface which was taken at this point. It was confirmed that most of the cells scattered outside the microchambers before the intermittent liquid feeding were now stored in the microchambers.

Taking the total number of the cells introduced to the flow path of the cell-spreading device as 100%, the number of the cells stored in the microchambers corresponded to 98%. That is, the cell recovery rate was 98%.

It is noted here that the cell recovery rate was calculated using the following equation: Number of recovered cells/Total number of cells×100(%). The total number of cells was determined by measuring the concentration of the cells in the cell suspension using a hemacytometer and converting the measured value based on the volume of the cell suspension introduced to the flow path.

Meanwhile, the number of recovered cells was determined by visually counting the cells under a microscope. Specifically, several microchambers in the flow path were selected and the cells retained therein were counted. Then, the average number of cells per microchamber was calculated, and the number of recovered cells was determined by multiplying the thus obtained average number of cells by the total number of chambers in the flow path.

Example 2

Figure 6:
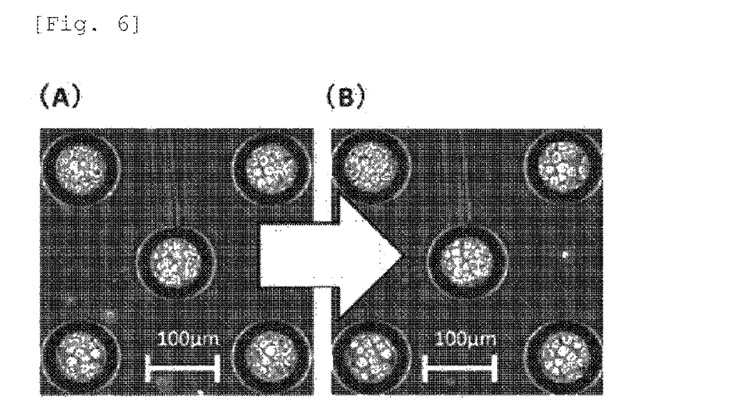
FIG. 6(A) is an enlarged image of microchambers after the step (Y) of Example 1, in which cells are stored in a layered state.
FIG. 6(B) is an enlarged image of microchambers after the step (Z) of Example 2, in which cells are in a single layer.

The step (Z) was carried out after the step (Y) of Example 1. That is, as the step (Z), 200 μL of PBS was continuously fed at a flow amount of 0.1 mL/min. As shown in FIG. 6, after the step (Y) of Example 1, the cells stored in some of the microchambers were in a layered form (FIG. 6(A); however, these cells were made into a monolayer by performing the step (Z).

Example 3

Figure 7:
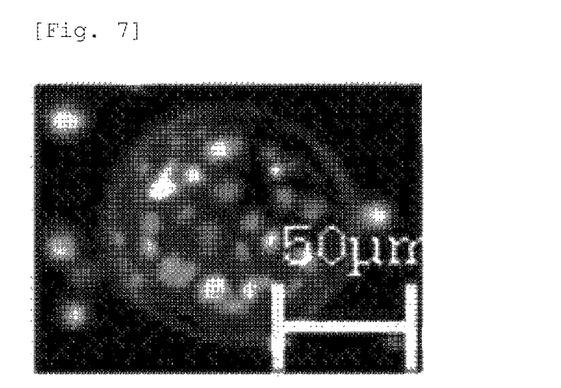
FIG. 7 is an enlarged image of a microchamber after the staining of Example 3.

After the step (Z) of Example 2, 200 μL of Hoechst 33342 stain was continuously fed at a flow amount of 0.1 mL/min. Three minutes later, the cells were observed under a microscope. The result thereof is shown in FIG. 7. This Hoechst 33342 stain was prepared by diluting "Hoechst 33342 10 mg/mL Solution in Water" manufactured by Molecular Probes Inc. in accordance with the manufacturer's instructions.

Although FIG. 7 shows only one microchamber, the number of stained cells corresponded to 90% of all cells introduced to the cell-spreading device.

Examples 4 to 6

The steps (W), (X) and (Y) were carried out in the same manner as in Example 1 except that a microchamber chip having microchambers whose bottom surface had been subjected to a UV-ozone treatment for 0 second, 30 seconds or 1 minute using a UV Ozone Cleaner manufactured by Meiwafosis Co., Ltd. was used in place of the microchamber chip of Example 1. Subsequently, as the step (Z), 200 μL of PBS was continuously fed at a flow amount of 10 mL/min.

Using a dynamic contact angle analyzer manufactured by FTA Inc. (FTA105), the contact angle between the UV ozone-treated microchambers and water (hereinafter, simply referred to as "the contact angle") was measured to be 70°.

When the cells were observed under a microscope, it was found that the cells were stably retained in the first layer stored in the microchambers.

TABLE 1

| Example | UV-ozone treatment time/Contact angle | Cell Recovery Rate (10 mL/min) |
|---|---|---|
| Example 4 | untreated/99° | 94% |
| Example 5 | 30 seconds/80° | 98% |
| Example 6 | 60 seconds/70° | 98% |

Example 7

The steps (W), (X) and (Y) were carried out and the cells were observed in the same manner as in Example 1, except that PBS containing 3 wt % of BSA was used in place of the PBS used in Example 1 and that the flow rate in the step (Y) was changed from 0.1 mL/min to 0.05 mL/min. As a result, by performing the intermittent liquid feeding at a lower flow amount, a cell recovery rate almost the same as that of Example 1 was achieved.

Example 8

As the step (Y) of Example 1, 1-minute shaking at 20 rpm using a shaker (Polymax 1040, manufactured by Heidolph Instruments GmbH & Co. KG) and subsequent 5-second standing were continuously repeated 10 times. As a result of observing the cells, it was found that a cell recovery rate almost the same as that of Example 1 was achieved without pump operation.

Comparative Example 1

Cells were observed in the same manner as in Example 1 except that the step (Y) was not carried out.

As a result, it was found that, in the same manner as shown in FIG. 5(A), a large number of cells were scattered outside the microchambers as well.

Thus far, embodiments and examples of the present invention have been described referring to the drawings; however, the present invention is not restricted to these embodiments and examples, and design modifications and the like can be made as long as they do not deviate from the gist of the present invention.

For instance, the flow path 5 is formed by the flow path-forming frame 2 and the microchamber chip 1; however, the constitution of the flow path 5 is not restricted thereto. That is, as long as the flow path is capable of allowing a cell suspension to flow therethrough on the microchamber chip 1, for example, the flow path 5 may be integrally and continuously formed by injection-molding of its wall and ceiling parts.

DESCRIPTION OF SYMBOLS

1: Microchamber chip
2: Flow path-forming frame
2a: Flow path top plate
2b: Flow path seal
3: Inlet
4: Outlet
5: Flow path
6: Microchamber
7: Height of flow path 5
10: Cell-spreading device
10A: Reservoir
11: Condenser lens
12: Emission filter
13: Pinhole member
14: Condenser lens
15: PMT
16: Chamber detection section
17: Computer
18: Rare cell-specifying section
19: Memory medium
20: Liquid-feeding pump (liquid-feeding device)
21: Liquid-feeding station
22: Sample
23: Diluent
24: Labeled antibody solution
25: Washing solution
26: Waste liquid container
27: Excitation light
28: Fluorescence
29: Reflected light
50: Optical detection system
100: Rare cell recovery system

The invention claimed is:

1. A method of recovering rare cells contained in a cell suspension, said method comprising:
providing a cell-spreading device formed on a microchamber chip, said cell-spreading device including an inlet, an outlet and an inner chamber intermediate and in fluid communication with said inlet and said outlet thereby providing a flow path for said cell suspension upon introduction of said cell suspension via said inlet, wherein a bottom surface of said inner chamber is defined by a surface of said microchamber chip having a plurality of recessed microchambers configured to store and retain cells;
a step (X) of spreading a plurality of cells on said microchamber chip by allowing via said inlet said cell suspension to flow in said flow path of said cell-spreading device, thereby creating a first group of cells positioned inside said recessed microchamber(s), and creating a second group of said cells positioned outside said recessed microchamber(s) on said surface of said microchamber chip; and
a step (Y) of performing intermittent liquid feeding to said inner chamber in which a cycle of feeding a liquid and stopping said feeding is alternated to provide an intermittent moving force that moves said second group of said cells, that is positioned outside said recessed microchamber(s), into said recessed microchamber(s), said moving force being applied in said flow path across said surface of said microchamber chip, whereby rare cells from said cell suspension can be recovered from said recessed microchamber(s).

2. The method of recovering rare cells according to claim 1, further comprising a step (W) of, before said step (X), wetting the surface of said microchamber chip by feeding thereto an aqueous solution having a surface tension lower than that of water.

3. The method of recovering rare cells according to claim 2, wherein the surface tension y of the aqueous solution is in the range 10 mN/m≤y≤60 mN/m.

4. The method of recovering rare cells according to claim 1, wherein, in said step (X), said cells are uniformly spread in said flow path on said microchamber chip by adjusting the flow rate of said suspension introduced to said flow path.

5. The method of recovering rare cells according to claim 1, wherein, in said step (Y), said alternated feeding liquid to said flow path is provided through the inlet port and the outlet port such that said cells positioned outside said recessed microchamber(s) are moved reciprocatively.

6. The method of recovering rare cells according to claim 1, further comprising a step (Z) of, after said step (Y), removing some of said cells stored in layers in said recessed microchamber(s) from said recessed microchamber(s) by continuously feeding a liquid at a flow rate which is the same as or higher than the maximum flow rate of said intermittent liquid feeding.

7. The method of recovering rare cells according to claim 1, wherein said rare cells are any one or more of circulating tumor cells [CTCs], circulating vascular endothelial cells [CECs] and circulating vascular endothelial precursor cells [CEPS].

8. The method of recovering rare cells according to claim 1, wherein said inner chamber providing said flow path is formed by arranging a flow path-forming frame integrally with said microchamber chip.

9. The method of recovering rare cells according to claim 8, wherein an upper surface and side surfaces of said inner chamber providing said flow path are defined by a surface of said flow path-forming frame.

10. A method of detecting rare cells, comprising:
recovering rare cells by the method of recovering rare cells according to claim 1; and
subsequently feeding a cell staining solution to said recessed microchamber(s) to perform cell staining and detection of said rare cells.

11. The method of recovering rare cells according to claim 1, further comprising the step of increasing an adhesive strength between a bottom of the microchamber(s) and said cells.

12. The method of recovering rare cells according to claim 11, wherein the step of increasing the adhesive strength includes subjecting a bottom of said microchamber(s) to a UV-ozone treatment in which UV is irradiated in the air, an oxygen-plasma treatment in which a plasma is irradiated in an oxygen atmosphere, or a coating treatment in which the bottom of said microchamber(s) is coated with a ligand.

13. The method of recovering rare cells according to claim 1, further comprising the step of subjecting the microchamber chip to a surface treatment that makes surfaces of the microchamber chip other than a bottom of the microchamber(s) non-adhesive to the cells.

14. The method of recovering rare cells according to claim 1, further comprising arranging a ceiling height of said inner chamber between a part of said surface of said microchamber chip outside said recessed microchamber(s) and a ceiling part of said inner chamber to be 50 µm to 500 µm.

15. The method of recovering rare cells according to claim 1, further including, after said step (X), allowing the cells to precipitate by leaving the cell suspension to stand for a predetermined period of time before performing said step (Y).

16. The method of recovering rare cells according to claim 15, wherein the predetermined period of time is 1 to 15 minutes.

17. The method of recovering cells according to claim 1, wherein said alternating cycle of feeding a liquid and stopping said feeding of said intermittent liquid feeding consists of a period of one-shot liquid feeding for moving said cells that are positioned outside of said recessed microchamber(s) and a standing period in which said cells are allowed to precipitate, the standing period is longer than the period of one-shot liquid feeding, wherein an amount of liquid moved during the one-shot liquid feeding is $1/100$-$1/2$ of a volume of said cell suspension in said flow path.

18. The method of recovering rare cells according to claim 1, wherein said step (Y) further comprises performing intermittent gas feeding, intermittent centrifuging of said microchamber chip, intermittent tilting of said microchamber chip, or intermittent application of vibration to said microchamber chip.

* * * * *